United States Patent [19]

Kesler et al.

[11] Patent Number: 4,875,366

[45] Date of Patent: Oct. 24, 1989

[54] APPARATUS AND METHOD FOR THE FIELD MEASUREMENT OF BEARING LUBRICANT AND SEAL INTEGRITY TESTING

[75] Inventors: John K. Kesler, Silver Spring; Robert J. McCown, Seabrook, both of Md.; John J. Shia, Richmond, Va.

[73] Assignee: ENSCO. Inc., Springfield, Va.

[21] Appl. No.: 221,597

[22] Filed: Jul. 20, 1988

[51] Int. Cl.⁴ ............................................ G01M 19/00
[52] U.S. Cl. ..................................... 73/118.1; 73/37; 73/149
[58] Field of Search ...................... 73/118.1, 149, 49.7, 73/37; 384/448; 184/108; 340/612, 613

[56] References Cited

U.S. PATENT DOCUMENTS

| | | | |
|---|---|---|---|
| 2,033,588 | 3/1936 | Pigott et al. | 265/10 |
| 3,072,896 | 1/1963 | Williams | 340/270 |
| 3,585,861 | 6/1971 | King | 73/432 |
| 3,623,372 | 11/1971 | Markey | 73/49.7 |
| 3,683,673 | 8/1972 | Eichler et al. | 73/37 |
| 3,946,593 | 3/1976 | Ruget | 73/10 |
| 3,962,916 | 6/1976 | Bouchy et al. | 73/149 |
| 4,000,656 | 1/1977 | Moidi | 73/432 R |
| 4,430,891 | 2/1984 | Holm | 73/149 |

*Primary Examiner*—Jerry W. Myracle
*Attorney, Agent, or Firm*—Sixbey, Friedman, Leedom & Ferguson

[57] ABSTRACT

The apparatus and method for the field measurement of bearing lubricant involves obtaining a control pressure value which is indicative of the pressure which would be generated by injecting a known, controlled volume of air or gas into a test bearing at the existing ambient temperature and pressure. Then, the same controlled volume of air or gas is injected through a valve controlled opening in the test bearing housing by an injection fixture which is sealed to the housing and which is connected to an injector for such controlled volume. Once the controlled volume is injected, the actual pressure in the test bearing is sensed and compared with the control pressure.

18 Claims, 2 Drawing Sheets

APPARATUS AND METHOD FOR THE FIELD MEASUREMENT OF BEARING LUBRICANT AND SEAL INTEGRITY TESTING

TECHNICAL FIELD

Grease or lubricant filled sealed bearings have been developed wherein the lubricant content of the bearing can only be determined by removing the bearing from service and subjecting the bearing to disassembly. The present invention provides a method and apparatus for field testing these bearings without disassembly.

BACKGROUND ART

Large bearing assemblies which have been developed for a variety of applications normally include grease fittings to permit the injection of grease or other lubricants into the bearing case. With such bearings, periodic attempts are made to inject additional lubricant into the bearing regardless of whether replenishment of the lubricant is actually required. This is both wasteful and time consuming, but has often proven to be the only method for insuring that a bearing remains properly lubricated short of complete bearing disassembly.

The problems involved in maintaining proper bearing lubricant supplies have been compounded by the development of permanently lubricated sealed bearings. Theoretically, these permanently lubricated sealed bearings are lubricated for life and consequently they are not provided with grease fittings to facilitate replenishment of the bearing lubricant. Practically however, such permanently lubricated sealed bearings also experience seal failure and lubricant leakage after long periods of use, particularly in harsh environments, and this condition is often difficult to detect unless the bearing is periodically disassembled for inspection. Periodic bearing disassembly and inspection is an extremely time consuming and expensive process for many bearing applications, as for example, in the case of railroad wheelset bearings. There is no method for effectively determining the grease content in the field of either a railroad wheelset bearing having a grease fitting or a permanently lubricated, sealed railroad wheelset bearing. To accomplish this, the wheelset must be removed from operation and disassembled for inspection.

To measure the lubricant content of a bearing in the field without disassembly, merely gaining access to the interior of the bearing case is not enough, for the grease or other lubricant will not be found in a single location to facilitate measurement. Instead, it will be splattered around within the closed interior of the bearing case.

Prior art devices have been developed to sense or measure the properties of bearing lubricant. U.S. Pat. Nos. 2,033,588 to Pigotti et al and 3,946,593 to Ruget show devices which are typical of those previously developed, but these units are not suitable for use in the field to measure the lubricant content of a sealed bearing.

The volume to be measured within a sealed bearing case is partially filled with liquid and the remainder is filled with air or gas. The volume within a closed container has been previously measured using a charge of air or gas, as illustrated by U.S. Patent Nos. 3,623,372 to Markey, 3,962,916 to Bouchy et al, 3,585,861 to Keng and 4,430,891 to Holm. These devices all disclose volume measurement techniques and devices which may operate effectively in controlled conditions, but which are not adapted for bearing field measurement conditions.

DISCLOSURE OF THE INVENTION

It is therefore a primary object of the present invention to provide a novel and improved method and apparatus for the field measurement of bearing lubricant and seal integrity testing which does not require the bearing to be disassembled or removed from service.

Another object of the present invention is to provide a novel method and apparatus for the field measurement of bearing lubricant which includes determining a control pressure value indicative of the pressure which would be obtained by injecting a controlled volume of air under pressure into a bearing having a minimal allowable lubricant content at ambient temperature and atmospheric pressure and subsequently injecting the same controlled volume of air into the bearing to obtain an actual pressure value for comparison with the control pressure value.

A further object of the present invention is to provide a novel method and apparatus for the field measurement of bearing lubricant which simultaneously tests the integrity of the bearing seals. The measurement and test procedure is normally achieved in a noninvasive manner by injecting air through the pressure release vent in the backing ring of a permanently lubricated sealed bearing or through the grease fitting of a nonpermanently lubricated bearing.

Yet another object of the present invention is to provide a novel and improved device for the field measurement of bearing lubricant which includes an interface head for sealing engagement with an external bearing surface having a projecting nozzle which permits air to flow freely into and out from a bearing casing.

A still further object of the present invention is to provide a novel and improved device for the field measurement of bearing lubricant which operates to obtain and register a control pressure value indicative of a pressure which would be obtained by injecting a controlled volume of air under pressure into the bearing under test if such bearing contained the minimal allowable lubricant content at the existing ambient temperature and atmospheric pressure. The device then vents the bearing under test and subsequently injects the same controlled volume of air into the bearing and registers the resultant pressure for comparison with the control pressure.

These and other objects of the present invention are achieved by obtaining a control pressure which is indicative of the pressure which would be generated by injecting a controlled volume of air or gas into a test bearing of a determined size containing an allowable amount of lubricant. The control pressure must be corrected for ambient temperature and atmospheric pressure. Subsequently, an equal volume of air or gas is injected into a test bearing and the actual bearing pressure is measured and compared with the control pressure. Also, the test bearing is maintained in a pressurized state to determine if a pressure drop indicative of seal leakage occurs. The test bearing is pressurized by a bearing lubricant measuring device having an air injection fixture for injecting air or gas into a bearing. The bearing fixture is mountable in airtight, sealed relationship on a bearing housing and is connected by a conduit to a cylinder having a chamber which can contain a known volume of air or gas. The conduit is provided with valving which opens or closes the conduit and which vents the conduit and the bearing to atmosphere. The conduit further includes a pressure sensing unit to sense the bearing pressure.

The chamber includes a piston operable from an air or gas source to force air or gas from the cylinder through the conduit and air injection fixture into the bearing under test.

BRIEF DESCRIPTION OF THE INVENTION

DETAILED DESCRIPTION OF THE PREFERRED EMBODIMENTS

Figure 1:
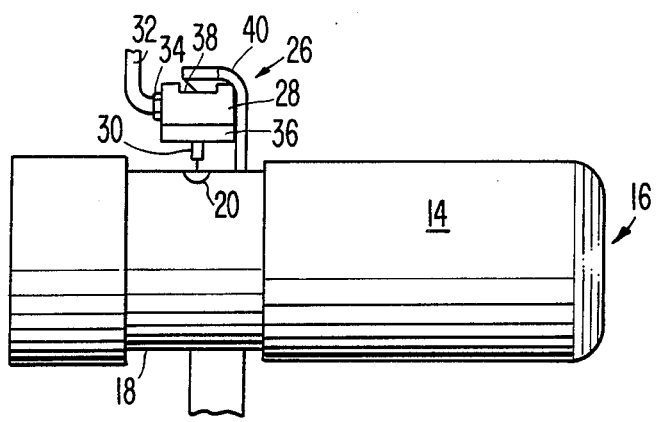
FIG. 1 is an exploded view in side elevation of an air injection fixture for the bearing lubricant measuring device of the present invention in combination with a test bearing.
Figure 2:
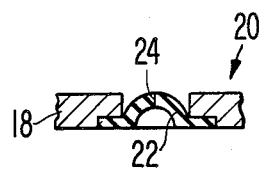
FIG. 2 is a sectional view of the pressure release vent for the test bearing of FIG. 1.
Figure 3:
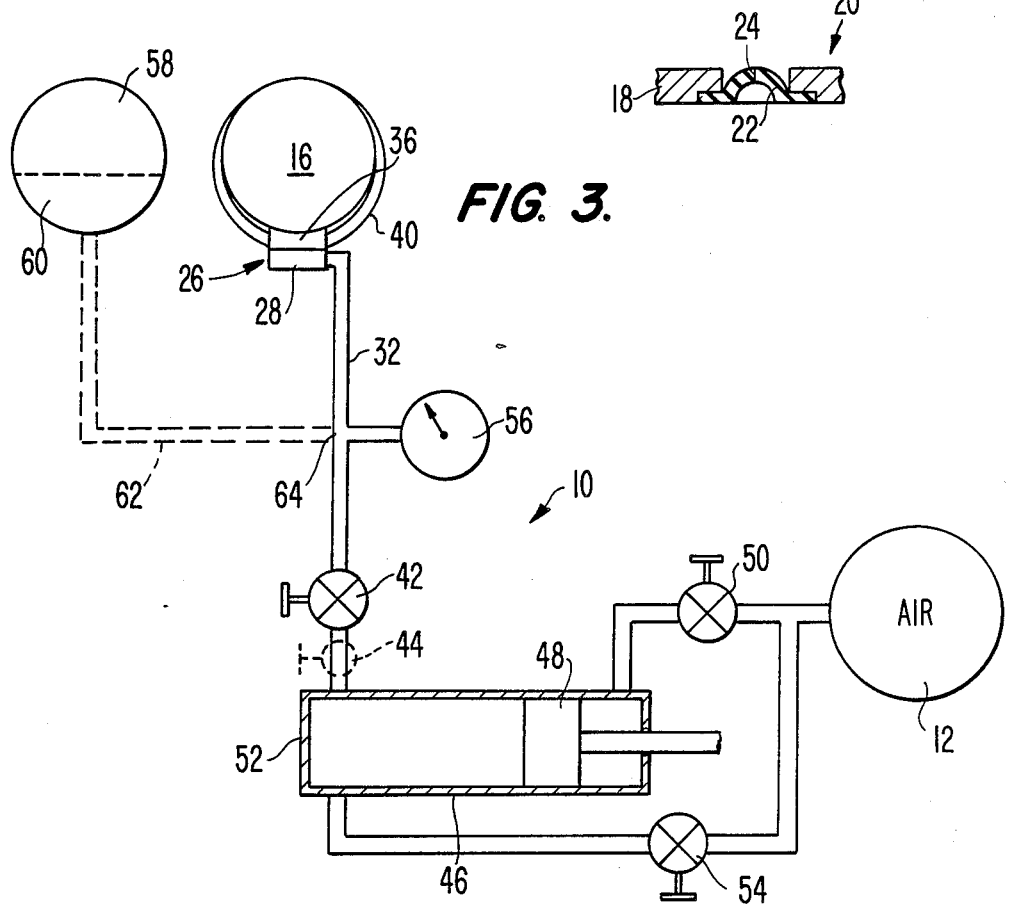
FIG. 3 is a diagrammatic view of the bearing lubricant measuring device of the present invention.

Referring to FIGS. 1, 2 and 3, the bearing lubricant measuring device of the present invention indicated generally at 10 includes a source of air or other pressurized gas 12 which is used to accomplish a measurement within the casing 14 of a bearing 16. This source of air or gas can be a supply of filtered shop air if a measurement is being taken in a repair shop. For other measurement applications, the source 12 may be a portable tank containing air under pressure or a portable supply tank connected to a portable compressor.

The bearing 16 has a backing ring 18 with a pressure release valve 20, as is conventional in many bearing constructions such as those used as the bearings for railroad wheelsets. The pressure release valve includes a dome-shaped rubber or resilient member 22 which is mounted to close an opening in the backing ring 18. A central slit 24 is formed in the member 22, and this slit is normally closed by the resilient nature of the member to seal the bearing casing 14. However, if the bearing heats up while in use and excessive pressure builds up inside the casing 14, the slit 24 is forced open by the pressure to provide a vent to the atmosphere.

The interface between the bearing lubricant measuring device 10 and the bearing casing 14 is critical, as an effective airtight seal must be provided. Often, this is made difficult by the rough cast surface of the bearing housing, but an effective seal can be made with an air injection fixture 26. This fixture includes a steel backing block 28 having a tube 30 projecting centrally from one surface thereof. The backing block is internally bored to connect the internal end of the tube 30 with a hose or air conduit 32 secured to the backing block by a fixture 34. Secured to the surface of the backing block and surrounding the tube 30 is a sealing layer 36 designed to form an airtight seal with the surface of the backing ring 18. Any suitable sealing layer material can be used, although a 1/16 to ⅛ inch thick layer of neoprene has been found to provide an effective seal.

The surface of the backing block 28 opposite the sealing layer 36 is provided with a transverse groove 38 to receive a strap 40. To position the air injection fixture 26 for use on a bearing 16, the tube 30 is inserted through the slit 24 in the pressure release valve 20. The strap 40 is then passed through the groove 38 and around the backing ring 18 and cinched tight to compress the sealing layer 36 against the backing ring to form an airtight seal around the tube 30. Any suitable known strap tightening means can be used to tighten and hold the strap 40, which can be a metal strap, or a chain which is tightened and held by a pair of chain vise grips.

Once the air injection fixture 26 is sealed in place on the backing ring 18 of a bearing 16, the internal pressure within the bearing is vented by a value 42 in the air conduit 32. This valve is a conventional three-way valve which in a first position, opens the conduit 32, in a second position closes the conduit, and in a third position, vents the conduit to the atmosphere. With this valve in the "vent" position, internal pressure from the bearing 16 passes through the tube 30 and the backing block 28 into the conduit 32 and out through the valve 42.

Instead of a three-way valve, the valve 42 could merely be a two-way valve to selectively vent the conduit 32 to the atmosphere. In this case, a second valve 44, shown in broken lines in FIG. 3, would be placed below the valve 42 to open or close the conduit. Once the bearing has been vented, the valve 42 is operated singly as a three-way valve or in combination with the valve 44 as a two-way valve to close the conduit 32 to the atmosphere while opening the conduit along its length. A known volume of air or other gas at a known pressure can now be forced into the bearing housing through the conduit 32. To accomplish this, a cylinder 46 of known volume having an internal piston 48 is employed. Although only one cylinder 46 is shown for purposes of illustration, it is possible to use a plurality of pneumatic cylinders connected in parallel with a series of control valves to permit an operator to select one, two or more cylinders. Air or gas under pressure from the source 12 is directed through a valve 50 into the area of the cylinder 46 behind the piston 48 to drive the piston from start position toward the end 52 of the cylinder. A second valve 54 remains closed, so that the piston forces air through the valve 42 (and valve 44), the air conduit 32 and the air injection fixture 26 into the casing 14. With knowledge of the bearing air volume, the amount of such bearing air volume which would be used by the minimum allowable grease content, and the amount of air injected at a known pressure into the bearing, it may be determined whether or not the bearing contains an acceptable amount of grease without removing the bearing from service. In fact, by injecting a known volume of air at a known initial pressure into the bearing, the air volume within the bearing can be calculated. Since the grease is relatively incompressible, the bearing air volume will remain the same while the air pressure within the bearing is increased. Once known, this air volume can be used to calculate the grease content of the bearing. The bearing air pressure can be read on a pressure gauge 56 which is in communication with the conduit 32.

Once the bearing is pressurized, the pressure is maintained for an interval to determine whether or not bearing seal leakage is occuring. If a steady pressure drop occurs once the bearing pressure has stabilized, seal leakage is indicated. Thus, once the piston 48 pressurizes the bearing, the valve 42 (or 44) may be operated to close the conduit 32 so that any pressure leakage must occur through the bearing seals.

Subsequent to obtaining a bearing pressure reading and seal check, the bearing is again vented using the valve 42 (or 44), and the line 32 is then closed. Now the valve 54 is opened to drive the piston 48 back to the start position. Valve 50, like valve 42, may be a three-way valve which closes off the line to source 12 while venting the cylinder 46 behind the piston 48 to atmosphere so that the piston may be returned to the start position. Obviously, the travel of the piston within the cylinder is limited so that air from the source 12 can drive the piston in both directions.

Unfortunately, the accuracy of measurements in the field taken with the bearing lubricant measuring device 10 are affected by changes in atmospheric pressure and temperature, since drops in either the ambient temperature or pressure reduce the final pressure value obtained from the bearing pressure measurement. To compensate for this, the bearing lubricant measuring device is first connected to a test cylinder 58 having an internal volume equal to the volume within the bearing housing under test. The test cylinder contains the minimum allowable volume of grease 60 for the bearing under test, and this cylinder is pressurized with the known volume of air to be subsequently applied to the bearing and a pressure reading is taken on the gauge 56. Subsequently, this pressure reading is used as a reference when the bearing is pressurize,, and this reference is accurate since the test cylinder is subject to the same ambient atmospheric pressure and temperature as the bearing.

The test cylinders 58 used for various bearing sizes may be provided with a valve similar to the pressure relief valve 20 to receive the tube 30 of the air injection fixture 26, or alternatively, a plurality of test cylinders of different sizes could be either permanently connected or releasably connectable to a fixture in the conduit 32 as illustrated by the broken lines 62 in FIG. 3. In the case of both a releasable and a permanent connection, a valve would be included in the conduit 32 between the connection point 64 and the air injection fixture 26 to selectively open and close the conduit 32. With the conduit closed, air would be provided to the test cylinder 58. If a plurality of test cylinders of different sizes are permanently connected in parallel to point 64, suitable valves would be provided to select the test cylinder to be pressurized.

Figure 4:
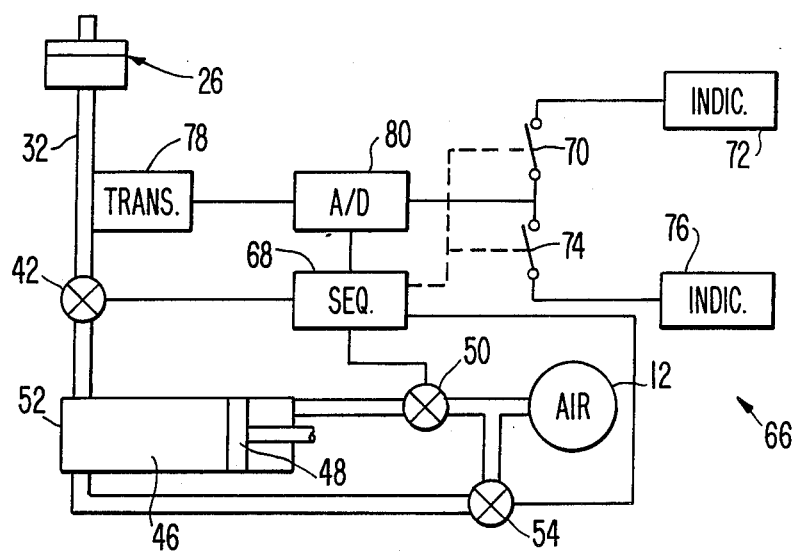
FIG. 4 is a diagrammatic view of a second embodiment of the bearing lubricant measuring device of the present invention.
Figure 5:
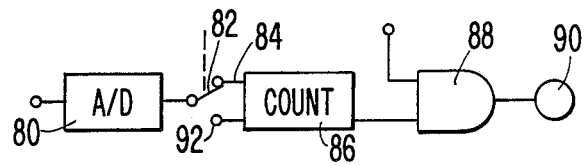
FIG. 5 is a block diagram of an indicator which can be used with the bearing lubricant measuring device of FIG. 4.
Figure 6:
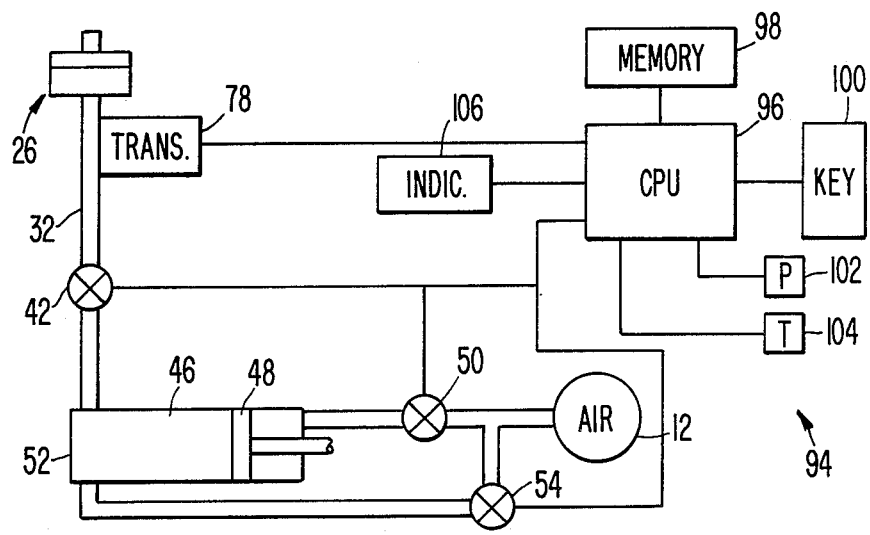
FIG. 6 is a diagrammatic view of a third embodiment of the bearing lubricant measuring device of the present invention.

The bearing lubricant measuring device 10 of FIG. 3 can be automated to a much greater extent than is shown in FIG. 3, as illustrated in FIGS. 4-6 where components which operate in the same manner as those previously described in connection with FIGS. 1-3 bear like reference numerals.

Referring now to FIG. 4, an automated bearing lubricant measuring device 66 is shown wherein the valves 42, 50 and 54 are operated in response to a sequencer 68. This sequencer can be any common electrical or electromechanical sequencer of known type which causes valves and switches to operate in a desired sequence. Such sequencers are commonly used on dishwashers, washing machines and similar appliances.

The sequencer 68 is adapted to control the bearing lubricant measuring device 66 through both a reference cycle and a measuring cycle in the manner previously described in connection with the bearing lubricant measuring device 10. Initially, with the piston 48 in the start position and the air injection fixture 26 mounted on a test cylinder 58, the sequencer is activated for a test cycle. This causes the valve 42 to open the conduit 38, the valve 50 to provide air to drive the piston from the source 12, and the valve 54 to close. The sequencer also closes a switch 70 to a first indicator 72 and opens a switch 74 to a second indicator 76.

A pressure transducer 78 replaces the pressure gauge 56 to sense the pressure in the conduit 32 and either the reference cylinder 58 or bearing 16. The output from the pressure transducer is converted in an analog to digital converter 80 and provided by the switch 70 to indicator 72 which registers the reference indication.

Once the reference indication has been registered, the sequencer closes the valve 42, closes the valve 50 to the source 12 but causes the valve to vent the cylinder 46 behind the piston 48, and opens the valve 54 to drive the piston to the start position. Now the switch 70 is opened, and the air injection fixture may be attached to a bearing.

With the piston 48 in the start position and the air injection fixture attached to a bearing, the sequencer 68 can be activated to perform a measuring cycle. The valves 50 and 54 are closed and the valve 42 vents the bearing to atmosphere. Subsequently, the valve 42 opens the conduit 32 and the valve 50 is opened to drive the piston 46 and pressurize the bearing. The pressure in the bearing is sensed by the transducer 78 and a signal indicative of the sensed pressure is provided by the analog to digital converter 80 and switch 74 to the indicator 76. The bearing pressure indication on the indicator 76 can now be compared to the reference indication on the indicator 72. If the reading on the indicator 76 begins to constantly decrease, seal leakage is present.

Once the bearing is pressurized, the sequencer causes the valve 42 to close the conduit 32 so that seal leakage can be sensed. Then the valve 50 is moved to the closed, vent position and the valve 54 is opened to return the piston 48 to the start position. Finally, the valves 52 and 54 are closed and the valve 42 is placed in the vent position to vent the bearing.

As illustrated in FIG. 5, the indicators 72 and 76 and the switches 70 and 74 can be replaced by a single indicator light system connected to the output of the analog to digital converter 80. During the test cycle, the sequencer 68 causes a switch 82 to connect the digital output from the analog to digital converter to a first terminal 84 of an up-down counter 86 causing the counter to count away from a reference point. The counter output in response to this count causes a gate 88 to power a red indicator light 98. When the measuring cycle is initiated by the sequencer 68, the switch 82 is moved to a second counter terminal 92, and the bearing pressure signal from the analog to digital converter decrements the counter 86. If the counter is driven below the reference point, the counter output switches the gate 88 to extinguish the red light 90 thereby indicating that the bearing lubricant is at an acceptable level. If, after a delay period, the red light comes back on, seal leakage is indicated.

It will be obvious that the counter output can be used to drive dual gates for a red and green indicator light. In this case, the red light would be illuminated when the counter is triggered in one direction from the reference point, and the red light would be extinguished and the green light illuminated when the counter passes through the reference point in the opposite direction.

FIG. 5 discloses an automated bearing lubrication measuring device 94 which is completely controlled by a central processor unit 96. This unit does not require the use of a test cylinder 58, for a memory 98 includes correction tables indicating the pressure error caused by various combinations of ambient temperature and pressure for various bearing volumes. The memory also includes tables indicating the pressure response for bearings of different volumes with an allowable level of lubricant. A keyboard 100 is used by an operator to enter the internal volume of a specific bearing under test into the processor 96. Ambient pressure and temperature sensors 102 and 104 respectively provide temperature and pressure indications which permit the processor to provide an accurate reference pressure for the bearing on an indicator 106. The processor then operates to sequence the valves 42, 50 and 54 during a subsequent measuring cycle to obtain an actual bearing pressure measurement for comparison with the reference measurement.

The present invention provides a novel method for rapidly ascertaining the grease content and seal condition of a bearing in the field without removing the bearing from service. By using either the test cylinder 58 or ambient pressure and temperature measurements with preprogrammed lookup tables, a control pressure can be obtained which is indicative of the pressure which would be generated by injecting a controlled volume of air or gas into a test bearing of a determined volume which contains an allowable amount of lubricant. Then the same volume of air is injected into the test bearing and the actual bearing pressure is measured and compared with the test bearing pressure. The bearing is maintained in a pressurized condition for a time interval after pressurization and the pressure value is observed to determine if a pressure drop due to seal leakage is present.

It has been found that many bearing pressurizing volumes are within the range of from 11 to 60 ounces, and that final pressure readings in such bearings of under 25 PSI are subject to error. Ideally, the best readings are obtained at pressures within the range of from 35 to 55 PSI. Changes in ambient temperature have a moderate effect on the accuracy of a final pressure reading, while changes in atmospheric pressure have a more dramatic effect upon accuracy.

INDUSTRIAL APPLICATION

The bearing lubricant measuring device and method of the present invention may be effectively employed in the field to measure the grease content of a bearing and to test bearing seals without removing the bearing from service. The device may be portable and is easily automated to provide a rapid and accurate test result in varying environments.

We claim:

1. A method for the field measurement of bearing lubricant in a test bearing which includes:
   obtaining a control pressure value indicative of the pressure which would be generated by injecting a controlled vehicle of air or gas into the test bearing with the test bearing containing an allowable amount of lubricant at the existing ambient temperature and atmospheric pressure,
   injecting the same controlled volume of air or gas into the test bearing, and
   subsequently obtaining a test pressure value resulting from the injection of the controlled volume of air or gas into the test bearing.

2. The method of claim 1 wherein the controlled volume of air or gas is sufficient to pressurize the test bearing to a test pressure value of at least 25 PSI or above.

3. The method of claim 1 wherein the controlled volume of air or gas is sufficient to pressurize the test bearing to a test pressure between 35 and 55 PSI.

4. The method of claim 1 wherein said test bearing includes a pressure release vent, said controlled volume or air or gas being injected through said pressure release vent and maintaining said pressure release vent open but sealed from the atmosphere to permit obtaining the test pressure value resulting from the injection of the controlled volume of air or gas.

5. The method of claim 1 which include s maintaining the controlled volume of air and gas in the test bearing for a test period and measuring the resulting test pressure valve during the test period to determine if a drop in the measured test pressure value occurs to indicate bearing seal leakage.

6. The method of claim 5 which includes recording a first test pressure value at the beginning of the test period, taking at least one subsequent test pressure value during the remainder of the test period, comparing said first test pressure value with said subsequent test pressure value and providing an alarm condition if said subsequent test pressure value is lower than said first test pressure value by more than a control amount.

7. The method of claim 5 which includes venting said test bearing to bring the pressure therein substantially to ambient atmospheric pressure before injecting said controlled volume of air or gas.

8. The method of claim 9 which includes venting said test bearing to bring the pressure therein substantially to ambient atmospheric pressure at the end of said test period.

9. The method of claim 10 wherein said test bearing includes a pressure release vent, said method including injecting said controlled volume of air or gas through said pressure release vent and venting said test bearing through said pressure release vent.

10. The method of claim 1 which includes venting said test bearing to bring the pressure therein substantially to ambient atmospheric pressure before injecting said controlled volume of air or gas.

11. The method of claim 1 which includes comparing the test pressure value to the control pressure value and providing an alarm indication if the test pressure value is lower than the control pressure value.

12. A method for the field measurement of bearing lubricant in a test bearing having a pressure release vent which includes sealing said pressure release vent from the ambient atmosphere, injecting a controlled volume of air or gas into the test bearing through the pressure release vent and subsequently holding the pressure release vent open while measuring the pressure within the test bearing resulting from the injection of said controlled volume of air or gas to obtain a test pressure value.

13. The method of claim 12 which includes venting said test bearing to bring the pressure therein substantially to ambient atmospheric pressure before injecting said controlled volume of air or gas.

14. The method of claim 13 which includes obtaining a control pressure value indicative of the pressure level within said test bearing at ambient temperature and atmospheric pressure which would occur in response to the injection of said controlled volume of air or gas if said test bearing contained a minimum allowable amount of lubricant and comparing said test pressure value to said control pressure value.

15. A measuring apparatus for measuring the lubricant in a test bearing having an enclosed bearing housing with a control valve controlled opening therein comprising injection fixture means adapted for mounting in sealed relationship on said bearing housing, said injection fixture means including an elongated, hollow projection for insertion through said control valve into said housing and inlet means in communication with said elongated hollow projection for providing air or gas thereto, conduit means connected to said inlet means, means connected to said conduit means for injecting a known control volume of air or gas under pressure through said conduit means, inlet means and hollow projection into said bearing housing and pressure measuring means connected to sense the pressure in said conduit means.

16. The measuring apparatus of claim 15 wherein valve means are provided in said conduit means for venting said conduit means to the atmosphere.

17. The measuring apparatus of claim 15 which includes register means for registering a control pressure value indicative of the pressure level within said test bearing at ambient temperature and atmospheric pressure which would occur in response to the injection of said control volume of air or gas if said test bearing contained a predetermined allowable amount of lubricant and the pressure sensed by said pressure measuring means in response to the injection of said control volume into said bearing ho sing.

18. The measuring apparatus of claim 17, wherein said register means includes indicator means operative to indicate when the pressure sensed by said pressure measuring means in response to the injection of said control volume into said bearing housing is less than said control pressure value.

* * * * *